United States Patent [19]

Reiland et al.

[11] Patent Number: 5,016,778
[45] Date of Patent: May 21, 1991

[54] SYSTEM FOR LOW COST DISPENSING OF SOFT PACKAGED ARTICLES

[75] Inventors: Kenneth H. Reiland; Mary J. Reiland, both of Apple Valley; Ronald J. Herold, Little Canada, all of Minn.

[73] Assignee: Four D, Incorporated, Apple Valley, Minn.

[21] Appl. No.: 196,984

[22] Filed: May 20, 1988

Related U.S. Application Data

[63] Continuation-in-part of Ser. No. 52,014, May 19, 1987, abandoned.

[51] Int. Cl.$^5$ ............................................. G07F 11/24
[52] U.S. Cl. ................................... 221/154; 221/232; 221/263; 221/281
[58] Field of Search ................. 221/1, 135, 154, 229, 221/232, 263, 281, 312 C; 206/495, 497, 823; 312/61, 71, 215, 217, 219; 194/350; 53/442

[56] References Cited

U.S. PATENT DOCUMENTS

| | | | |
|---|---|---|---|
| 1,452,456 | 4/1923 | Crupain | 206/495 X |
| 1,879,884 | 9/1932 | Rowe | 194/350 X |
| 2,573,827 | 11/1951 | Bigelow | 206/495 X |
| 2,807,362 | 9/1957 | Haddad | 206/495 |
| 2,821,329 | 1/1958 | Casey et al. | 221/232 X |
| 3,343,898 | 9/1967 | Larson | |
| 3,969,580 | 10/1972 | Saltzer | 53/442 |
| 4,046,243 | 9/1977 | Valentine | 221/102 X |
| 4,133,421 | 1/1979 | Hanley et al. | 221/232 X |
| 4,477,130 | 10/1984 | Frantz | 312/219 |
| 4,706,845 | 11/1987 | Schnurer et al. | 221/102 |

Primary Examiner—F. J. Bartuska
Attorney, Agent, or Firm—Merchant, Gould, Smith, Edell, Welter & Schmidt

[57] ABSTRACT

A system and method is provided for low cost dispensing of soft packaged articles. The soft packaged articles each include an internally positioned forming member. The forming members and articles are enclosed in heat shrinked material so that each soft packaged article is uniformly shaped above and below the forming member. A dispenser for holding and dispensing one soft packaged article at a time is also provided.

1 Claim, 4 Drawing Sheets

SYSTEM FOR LOW COST DISPENSING OF SOFT PACKAGED ARTICLES

BACKGROUND OF THE INVENTION

This application is a continuation in part of application Ser. No. 052,014, filed May 19, 1987 by one of the applicants, which is now abandoned.

TECHNICAL FIELD OF THE INVENTION

The present invention relates generally to the field of vending machines, and more particularly to a vending machine for dispensing soft packaged articles.

Within the field of vending machines, there exists a need for tamper resistent dispensers which are precision constructed to avoid jamming of the dispensed articles. Further, there exists a need for a compact and efficiently loaded vending dispenser which permits reliable dispensing of soft packaged articles, such as diapers or other hygienic materials.

A variety of vending machines have evolved. Typically, articles in a vending machine dispenser are arranged for gravity feed type of dispensing actuated by coin operated payment means. Often such articles are arranged on horizontal tab mean, roller drums, or in stacked relation with other articles. Frequently, articles which are stacked are packaged in boxes or other hardened enclosures to facilitate dispensing by preventing jamming at the point of dispensing. However, significant inefficiencies occur when using hardened enclosures, referred to herein as hard packaging or hard packaged articles. Principally, such hard packaging is costly and occupies volume within the dispensing which could be used more efficiently. A related problem involves improper discarding of the hard packaging causing environmental pollution and similar problems Another technique for dispensing articles permits soft packaging around the article. Typically, such soft packaged articles are not efficiently stored for dispensing because of a requirement for individually mounting each article on a tab or other mounting means. Alternate arrangements for soft packaged articles may include stacking, however, such configurations often result in jamming or other forms of malfunction of the dispenser. This may be caused by imprecisely oriented articles or by adjacent soft packaged articles which have become frictionally attached. Similar undesirable results occur when soft packaged articles are not of uniform dimensions.

Yet another problem exists with vending machines relating to vandalism or other unauthorized access to the contents therein. Often when machines are tampered with, the effect is to prevent further vending operation until substantial repairs have been accomplished. Such repairs may involve substantial expenditures and may result of lost revenues due to inoperation of the vending machine. Other forms of undesirable access may include attempts to contaminate the products contained within the dispenser.

Yet another problem relates to costly methods of manufacturing and assembling internal components of dispensers for vending articles. Often such components are cut or manufactured from different grade materials and from different sheets or lots. Moreover, substantial assembly costs may occur due to welding and otherwise connecting the various components. Additionally, most vending machine internal components are not readily removed or replaced by alternate choice components due to the extensive time and damage which would result. Such inflexibility results in narrow utility with respect to alternate shaped goods which might otherwise be dispensed using the identical exterior housing and location of the machine.

Yet another problem occurs due to vending machines which must be located in areas having enough room to accommodate the generally bulky sized dispensers. A related problem exists with dispensers which must be located near electrical power sources for proper operation.

What has been needed therefore has been a compact dispensing machine which is capable of mechanically dispensing consistently accurate quantities of soft packaged articles. Moreover, a need exists for such a dispensing machine which efficiently stores the articles in an improved tamper resistent environment.

What has been further needed is a dispensing machine for soft packaged articles which includes internal components which are more economically manufactured from a single sheet and grade of material and which may be more efficiently assembled or selectively removed and replaced by authorized personnel without affecting the appearance or physical integrity of the exterior.

What has been further needed has been a low cost method for manufacturing and dispensing soft packaged articles.

These and other problems are solved by the present invention. Yet other objects and advantages will become apparent from the following descriptions, taken in connection with the accompanying drawings wherein are set forth by way of illustration certain embodiments of the present invention.

SUMMARY OF THE INVENTION

A low cost system for dispensing soft packaged articles is provided. The system comprises a plurality of soft packaged articles, such as packaged diapers or other plaint articles, which includes a precision cut forming means placed with them. Tension wrapped and heat shrinked protective means then encloses the article and the forming means to provide soft packaged articles with uniform cambered crown shapes. A precision cut modular dispenser is also provided for holding and selectively releasing one soft packaged article at a time.

The drawings constitute a part of this specification and include exemplary embodiments of the present invention, while illustrating various objects and features thereof. It will be understood that in some instances relative material thicknesses and relative component sizes may be shown exaggerated, to facilitate an understanding of the invention.

BRIEF DESCRIPTION OF THE DRAWINGS

While the specification concludes with claims particularly pointing out and distinctly claiming the subject matter as forming the present invention, it is believed that the invention will be better understood from the following description taken in connection with the accompanying drawings in which.

DETAILED DESCRIPTION WITH PREFERRED EMBODIMENTS

As required, detailed embodiments of the present invention are disclosed herein. It is to be understood however, that the disclosed embodiments are merely exemplary of the invention, which may be embodied in various forms. Therefore, specific structural and functional details disclosed herein are not to be interpreted as limiting, but rather as a basis for the claims and as a representative basis for teaching one skilled in the art to variously employ the present invention in virtually any appropriately detailed system or structure.

Figure 1:
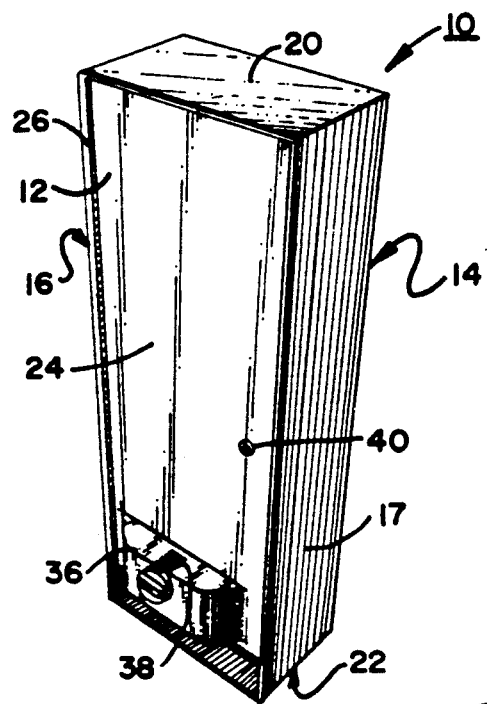
FIG. 1 is a perspective view of a preferred embodiment soft packaged article dispensing means with the front access door in the closed position.

Referring to FIGS. 1-7, the reference numeral 10 generally designates a precision cut modular dispenser according to the present invention. In FIG. 1, a dispenser 10 is illustrated including: inner and outer faces of a front surface 12, a back surface 14, side surfaces 16, 17, a top surface 20, and a bottom surface 22. Preferably, an access door 24 is located in a portion of front surface 12 and is movably mounted on a recessed hinge portion 26 between an open and closed position. The outer face of dispenser 10 is preferably constructed and arranged with a smooth appearance which is resistant to tampering or vandalism, e.g. without readily visible means for prying open any of the various surfaces. The enclosure thus formed by the above described surfaces constitutes a housing 28 which encloses and provides means for dispensing malleable or pliants articles 29, such as diapers, which have been precision soft packaged. The housing 28 therefore protects internal components and soft packaged articles 30, shown in FIG. 2, for dispensing. As shown dispenser 10 presents a compact and non-jagged appearance.

As depicted in FIG. 1, housing 28 further includes a dispensing chute lower opening 34 defined by the front surface 12 beneath access door 24. Dispensing chute lower opening provides a location for retrieval of each dispensed soft packaged article 30 following actuation of coin operated payment means 36. Preferably, coin operated payment means 36 presents a non-jagged outer surface for safe and easy operation. Further, payment means 36 may be constructed utilizing conventional coin mechanisms or of other configurations which allow dispensing of articles 30 when properly actuated. Preferred embodiment payment means 36 includes receptacles 38 for insertion of up to eight coins, although more or less may be desirable.

FIG. 1 also illustrates means for preventing tampering with the articles 30 enclosed within housing 28. For example, hinge portion 26 is recessed behind the plane including the outer face of front surface 12 to resist any effort to tap or pry the hinge from housing 28 or to remove access door 24. Also, by spacing recessed hinge portion 26 away from side surface 16, any attempt to tamper therewith via side surface 16 would necessitate penetration of several layers of housing 28 material. Accordingly, attempts at tampering or unauthorized access to the contents of housing 28 are discouraged. Moreover, the compact size of preferred dispenser 10 permits flush mounting of the dispenser between such mounting may further prevent any attempts at vandalizing dispenser 10. It is also recognized that the superior tamper resistent means of dispenser 10 permits its use in non-flush mounted settings as well. A key operated lock mechanism 40 is also preferably provided for selectively moving access door 24 between open and closed positions and thereby gaining or preventing access to the interior of dispenser 10.

Figure 2:
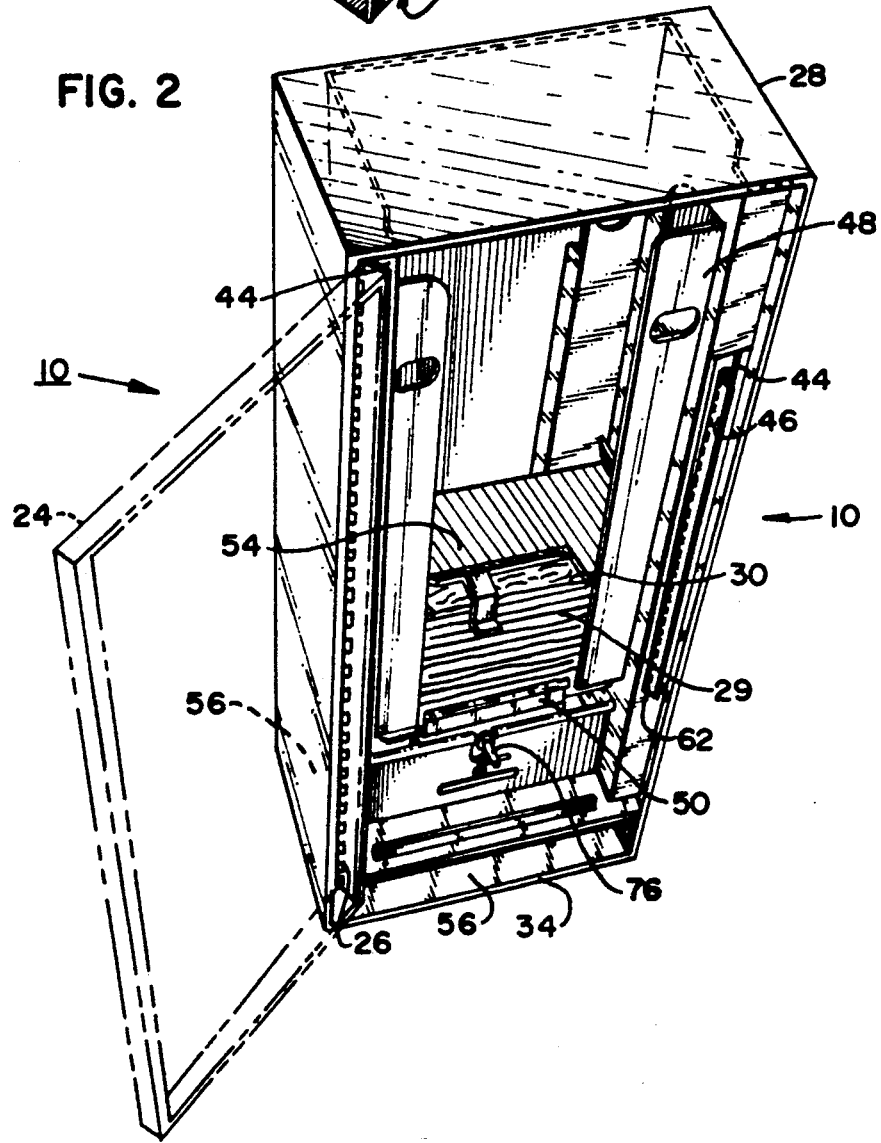
FIG. 2 is a perspective view of a partially preferred embodiment soft packaged article dispensing means with the front access door in the open position illustrating the modular internal components and the tamper resistant chassis latch means.
Figure 7:
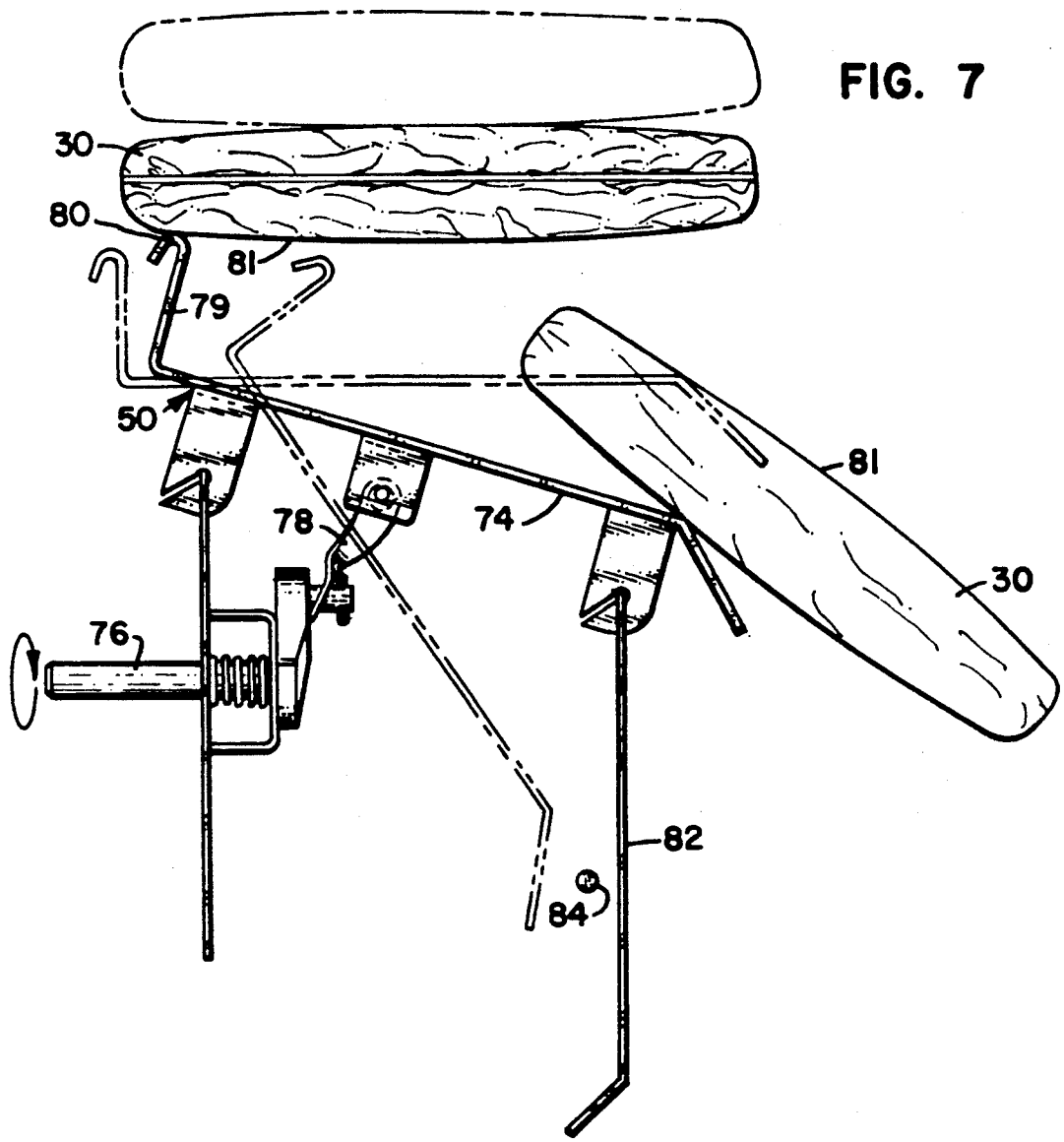
FIG. 7 is a side elevation view of a preferred flapper means and vertically stacked soft packaged articles illustrated in a dispensing cycle where the flapper means moves from a first retaining position to a second release position, illustrating the relation between the cambered crown shaped soft packaged articles and the flapper means vertical member.

FIG. 2 is a perspective view of a preferred dispenser 10 with access door 24 shown in an open position. FIG. 2 illustrates various internal structural features and components of dispenser 10 as well as a plurality of vertically stacked soft packaged articles, such as diapers or other pliable products. More specifically, FIG. 2 shows hinge mounting surface 44, chassis latch means 46, vertical stacking means 48, flapper means 50, and biasing means 54. In operation, coin operated payment means 36 is coupled to flapper means 50. Therefore, when payment means 36 is operated, flapper means 50 is cycled between a first retaining position, as shown in FIG. 2, and a second release position, as shown in FIG. 7. Preferably, flapper means 50 then releases a single soft packaged article into a dispensing chute 56 beneath flapper means 50 permitting access to the dispensed article through dispensing chute lower opening 34.

Although a variety of vending machine dispensers are currently known in the art, particular problems exist with respect to dispensing soft packaged articles. Indeed, a common difficulty with soft packaged article is the tendency of these items to frictionally attach and then jam the dispensing mechanism within a dispenser. Other problems result from non-uniform sizing of such products or irregular shaping of the packages. Yet other difficulties arise from uneconomical packaging of articles which are to be rendered. These and other problems in the art are solved by the present invention through precision manufacturing of soft packaged articles 30 having uniform cambered crown shapes. The dispensing cycle will be further discussed in detail in relation to FIGS. 5-7.

FIG. 2 illustrates further means for preventing tampering with or unauthorized access to the contents of housing 28. As shown, chassis latch means 46 is hingably mounted on hinge mounting surface 44. Preferably, hinge mounting surface 44 is constructed by low cost bending of portions of housing 28 during manufacture to provide a surface which is oriented peripherally around a recessed portion of front surface 12 for receipt of access door 24 in the closed position. Preferably, chassis latch means 46 comprises an elongate plate which is securely mounted to latch hinge means 62 on hinge mounting surface 44. It is observed that chassis latch means 46 extends along a substantial length of access door 24.

Figure 3:
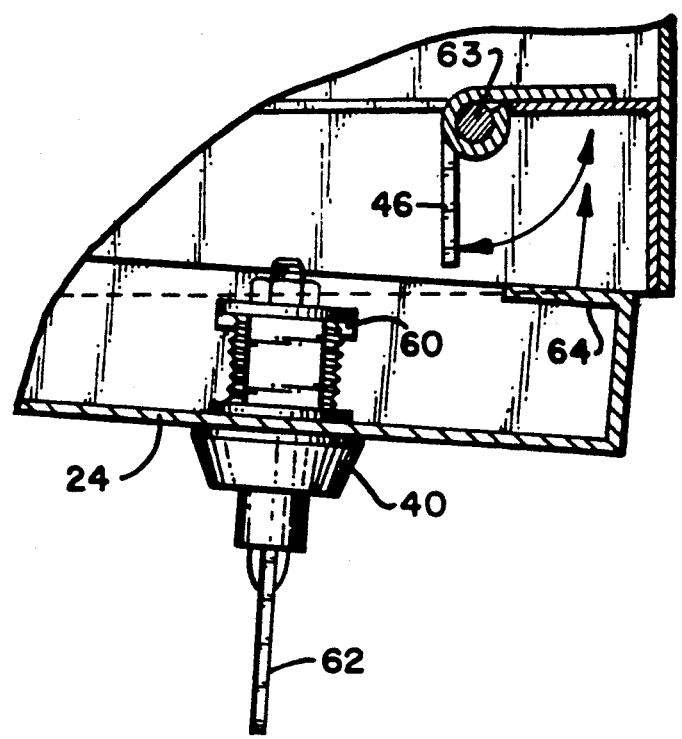
FIG. 3 is a fragmentary top plan view of a preferred chassis latch means in an open position.
Figure 4:
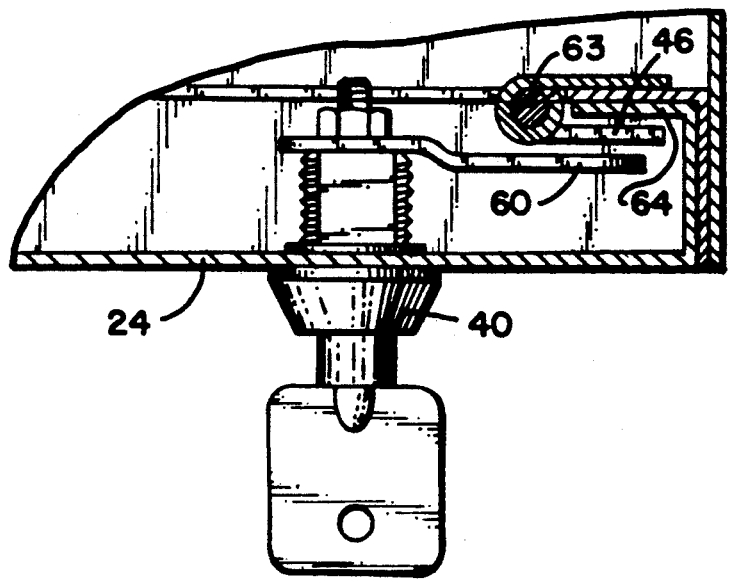
FIG. 4 is a fragmentary top plan view of a preferred chassis latch means in the closed and latched position.

FIG. 3 illustrates a top plan view of chassis latch means 46 corresponding generally to the open position shown in FIG. 2. Referring to FIG. 3, access door 24 key operated lock mechanism 40 may be seen. Key operated lock mechanism 40 includes cam member 60 which is operably rotated by key member 62 from an unlocked position to a locked position. As further illustrated in FIG. 4, access door 24 comprises receiving lip 64 constructed and arranged for receipt of chassis latch means 46 which is rotated on latch hinge means 62 by cam member 60 to a locked position as shown in FIG. 4. The locked position of chassis latch means 46 thus imparts vertical strengthening force to a substantial portion of access door 24 rather than merely that portion of access door 24 proximate key operated lock mechanism 40 as is more prevalent in other types of vending dispensers.

Referring again to FIG. 2, it is observed that the hinge mounting surface 44 provides means for convenient mounting of all internal components of dispenser 10. Accordingly, removal and replacement of such components may be more readily accomplished if so desired. Further, the modular construction of dispenser 10 permits manufacturing of internal components from single sheets of metal material utilizing known methods of easy shearing and conventional bending means. This further enhances the cost of constructing dispensers 10 for use in the system of the present invention. Additionally, heat treating, zinc plating, or galvanizing of internal components may further enhance the durability of the materials.

FIG. 5 is a top plan view of a preferred embodiment soft packaged article 30 according to the present invention. Although differently shaped articles may be utilized in correspondingly shaped dispensers, preferred soft packaged article 30 is rectangularly shaped. Soft packaging according to the present invention includes use of precision cut forming means 68 constructed and arranged for placement within individual articles 29. Forming means 68 may comprise a forming member 69 in the shape of a plate or tray having an upper surface, a lower surface, and faired corner portions. A preferred material includes cardboard, however other materials may be utilized to achieve the advantages of this invention. Packaging of articles 29 in relation to forming member 69 may include placing forming member 69 within a fold of article 29 and placing protective means 72 completely around both the forming member 69 and article 29. Although protective means 72 may be comprised of various materials, it is preferable to utilize lightweight and clear packaging material. Preferably, such material has a low coefficient of friction and may be safely exposed to heat shrinking techniques. The frictional coefficients of such materials are important in the selection process in order to minimize any frictional attachment between adjacently oriented soft packaged articles 30.

Figure 5A:
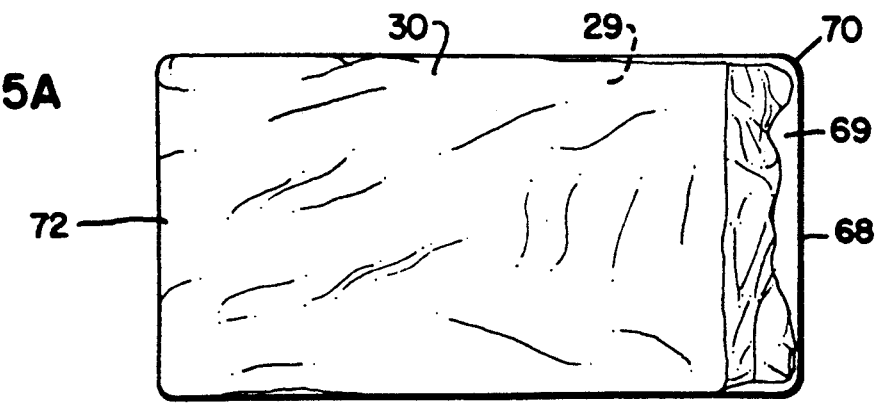
FIG. 5A is a top plan view of a precision cut soft packaged article.
Figure 5B:
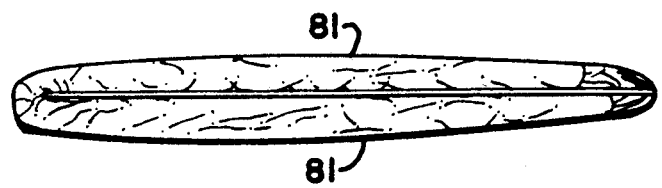
FIG. 5B is a side elevation view of a cambered crown shaped soft packaged article.

Preferably, soft packaged article 29 is tension wrapped and exposed to heat shrinking. Faired corner portions 70 assist in preventing tearing of protective means 72 during the heat shrinking process. Protective means 72 is placed around forming member 69 and article 29 so that the tension created by shrinking and the manner of placing article 29, and any other articles, on forming member 69 creates soft packaged articles 30 which are substantially equally shaped both above the top surface and below the bottom surface of forming member 69, as depicted in FIG. 5B. Preferably, this results in uniform shaped soft packaged articles having cambered crown portions. By utilizing precision cut forming members 69 with protective means 72, substantial packing efficiencies and improved tolerances may be realized. Moreover, the spacing between vertical stacking means 48 may be within more precise tolerances and therefore facilitate more reliable dispensing of soft packaged articles 30 when the soft packaged articles are precisely dimensioned. Futher economies are achieved by placement of the forming member 69 within the folded article 29 to be dispensed, rather than on the outside as is taught in the prior art.

It should be emphasized that soft packaged article vending reliability is more consistently achieved by providing soft packaged articles 30 which each have a convex cambered crown shape. The cambered crown shape, illustrated in FIGS. 5B-7 permits reduced surface area contact between adjacently placed articles, thus aiding in the dispensing of only one soft packaged article from the dispenser during any one dispensing cycle.

Figure 6:
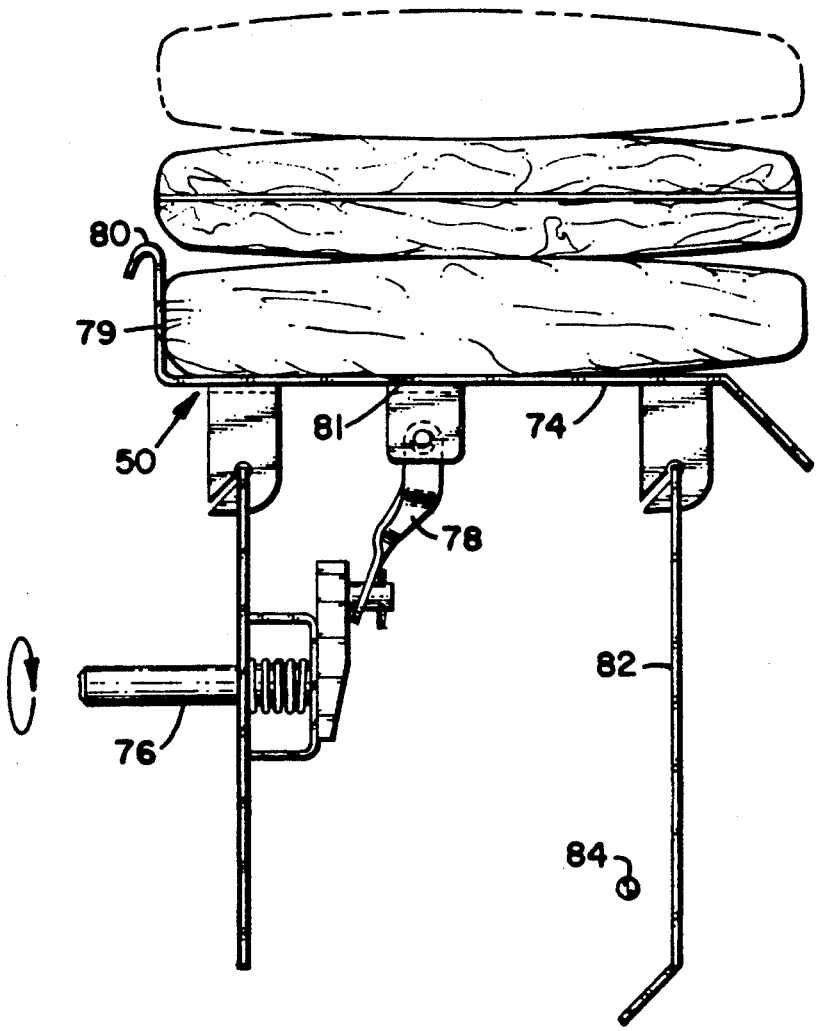
FIG. 6 is a side elevation view of a preferred arrangement of soft packaged articles vertical stacked on a flapper means horizontal support surface in the retaining position.

As illustrated in FIGS. 6-7, soft packaged articles 30 are preferably vertically stacked above flapper means 50. Each successive soft packaged article 30 to be dispensed rests on flapper means 50 horizontal support surface 74 when flapper means 50 is in the first retaining position. The first retaining position preferably corresponds to horizontal support 74 surface being generally perpendicularly oriented to vertical stacking means 48. As the movement of flapper means 50 from the first retaining position to the second release position occurs, one soft packaged article 30 is dispensed into dispensing chute 56. Initiation of dispensing occurs when coin operated payment means 36, which is coupled with flapper means coupling member 76, is actuated and rotated. As flapper means coupling member 76 rotates, flapper arm 78 pulls horizontal support surface 74 in the downward direction. Although soft packaged articles 30 may begin to release from horizontal support surface 74 at various angles and under various weights, testing of preferred precision cut modular dispenser 10 indicates initiation of release at a downward angle of horizontal support surface 74 of about 15 degrees. Further, the shortened length and position of flapper arm 78 relative to horizontal support surface 74 permits steep angles to be achieved in order to facilitate release of soft packaged articles 30. Indeed, preferred flapper means 50 may achieve release angles of approximately 55 degrees. Also, horizontal support surface may include treated surface material to further assist in dispensing.

As one soft packaged article 30 dispenses into dispensing chute 56, the flapper means vertical member 79, with rolled upper edge 80, is positioned beneath the cambered surface of the next soft packaged article 30 is dispensed during each flapper means cycle between the flapper means 50 first and second positions. Soft packaged articles which are vertically adjacently stacked and which do not have the uniform shape and preferred camber of soft packaged articles 30 may cause jamming or other malfunctions vend of a vending dispenser. Vending reliability and reduction of overall cost if further achieved by utilizing a preferred dispensers 10 which is mechanical and without any electrical components or requirements. Security gate means 82 and stop means 84 further prevent tampering or unauthorized removal of the contents of preferred modular dispenser 10.

A low cost method for dispensing soft packaged articles 30 from a dispenser 10 is also disclosed by the present invention. This method includes providing a precision dimensioned soft packaged article 30 comprising: a precision cut forming member 69 in the preferred shape of a plate or tray having an upper surface, a lower surface, and faired corner portions 70, as shown in FIG. 5A; a plaint article 29 to be dispensed which is folded around forming member 69 upper and lower surfaces; and protective means 72 which in tension wrapped and heat shrinked around forming member 69 and article 29 so that soft packaged article 30 is substantially equally shaped in the cross section above and below forming member 69 in the shape of a cambered crown 81. The method further includes placing a plurality of uniformly dimensioned soft packaged articles 30 in stacked relation so that cambered crown portions 81 of adjacent soft packaged articles 30 are in contact. Then, flapper means 50, shown in FIGS. 6–7, is actuated to dispense one soft packaged article 30 while simultaneously retaining the remaining stacked articles 30 by moving a portion of flapper means 50 beneath the cambered surface and contacting crown portion 81 of the next stacked article 30 to be dispensed.

The preferred method may also include the further step of placing fragrant powder means, such as talcum or baby powder, between crown portions 81 of adjacent soft packaged articles 30. This promotes ease of dispensing as well as providing pleasant odors in the vicinity of dispenser 10 and articles 29.

Accordingly, a tamper resistant low cost system and method for mechanically dispensing one soft packaged article at a time is provided. Utilization of precision cut forming members 69 placed within plaint articles 29 rather than all around the outside of articles 29 provides substantial advantages. A system according to the present invention may be provided which is compact and which has modularized components for more convenient replacing or upgrading. Superior tamper resistent means provide further reliability of this dispensing system.

It is to be understood that while certain embodiments of the present invention have been illustrated and described, the invention is not to be limited to the specific forms or arrangements of parts described and shown above, since others skilled in the art may devise other embodiments still within the limits of the claims.

What is claimed is:

1. A tamper resistant low cost system for mechanically dispensing soft packaged articles comprising:
   a) a plurality of soft packaged articles having:
      i) precision cut forming means constructed and arranged for attachment and precise shaping of a pliant article thereon; the forming means comprising a forming member constructed in the shape of a flat plate having an upper surface, a lower surface, and fared corner portions; the forming member comprising means for folding one of the articles over the forming member upper surface and lower surface;
      ii) tension wrapped and heat shrinked protective means enclosing each article and each forming member; the protective means being placed around the article and the forming member so that the soft packaged article is substantially equally shaped in the cross section above the top surface and below the bottom surface of the forming member;
      iii) the forming means and the protective means providing soft packaged articles having a uniform and predetermined shape wherein each of the soft packaged articles comprises a convex cambered crown shape above and below the forming member, the cambered crown shape permitting reduced surface area contact between adjacent articles and therefore substantially aiding the dispensing of only one soft packaged article at a time;
   b) a precision cut modular dispenser having means for holding and selectively releasing one soft packaged article at a time, the dispenser comprising:
      i) housing means for enclosing the soft packaged articles having an enclosure with a dispensing chute lower opening, the enclosure having inner and outer faces including a front surface with an access door, a back surface, a pair of side surfaces, a top surface, and a bottom surface, the enclosing outer face having a smooth appearance resistent to tampering, and the dispensing chute lower opening being defined by the housing front surface beneath the access door, the dispensing chute lower opening providing a location for accessing the dispensed article;
      ii) stacking means for maintaining vertical stacking and alignment of soft packaged articles;
      iii) flapper means beneath the stacking means comprising a horizontal support surface, a vertical member, actuating arm means, and depending security gate means, the flapper means having a first retaining position and a second release position per operating cycle, in the first retaining position each successive soft packaged article to be dispensed rests on the flapper means horizontal support surface; and the movement of the flapper means from the first retaining position to the second release position dispenses one soft packaged article and positions the flapper means vertical member beneath the cambered surface of the next soft packaged article so that only one soft packaged article is dispensed during each flapper means operating cycle;
      iv) biasing means for urging the soft packaged articles toward the flapper means and for maintaining the forming member in each soft packaged article in a plane consistently oriented in relation to the stacking means and for preventing the operation of the flapper means when all soft packaged articles have been dispensed;
      v) coin-operated payment means coupled to the flapper means for receiving payment for each article and for permitting actuation of the flapper means between the first and the second positions;
      vi) a dispensing chute for receiving a soft packaged article released from the flapper means; and
   c) means for preventing tampering with the soft packaged articles within the modular dispenser comprising:
      i) an access door recessed hinge portion located within the front surface of the housing, the recessed hinge portion being spaced away from a side surface of the housing and being constructed and arranged for permitting selective movement of the access door between open and closed positions;

ii) chassis latch means extending substantially the entire vertical length of the access door, the chassis latch means including:
   a) a key operated lock mechanism located on the access door; and
   b) a chassis latch member hingably mounted within the housing, the chassis latch member being moved into locking engagement with the access door by operation of the lock mechanism;

iii) mounting lip means for securely mounting the stacking means and the flapper means within the housing enclosure independent of any requirement for penetrating the outer surface of the enclosure;

iv) security gate means attached in depending relation from the flapper means horizontal support surface, the security gate means providing protection to the articles within the housing from unauthorized removal through the dispensing chute lower opening.

* * * * *